United States Patent [19]

Rink et al.

[11] 4,328,214
[45] May 4, 1982

[54] CYCLOPEPTIDES AND PHARMACEUTICAL PREPARATIONS THEREOF AND ALSO PROCESSES FOR THEIR MANUFACTURE

[75] Inventors: Hans Rink, Riehen; Peter Sieber, Reinach; Bruno Kamber, Arlesheim, all of Switzerland

[73] Assignee: Ciba-Geigy Corporation, Ardsley, N.Y.

[21] Appl. No.: 162,712

[22] Filed: Jun. 25, 1980

[30] Foreign Application Priority Data

Jul. 4, 1979 [CH] Switzerland .................. 6243/79
Feb. 12, 1980 [CH] Switzerland .................. 1135/80

[51] Int. Cl.³ .................. A61K 37/00; C07C 103/52
[52] U.S. Cl. .................. 424/177; 260/112.5 S
[58] Field of Search .................. 260/112.5 S; 424/177

[56] References Cited

U.S. PATENT DOCUMENTS 3,725,380 4/1973 Konig et al. .
3,862,113 1/1975 Riniker et al. .
3,875,207 4/1975 Iselin et al. .
3,944,590 3/1976 Iselin et al. .
4,238,481 12/1980 Rink et al. .

FOREIGN PATENT DOCUMENTS 1295 9/1978 European Pat. Off. ............ 424/177

*Primary Examiner*—Delbert R. Phillips
*Attorney, Agent, or Firm*—Prabodh I. Almaula

[57] ABSTRACT

The somatostatin-analogous cyclic octapeptides according to the invention of the general formula

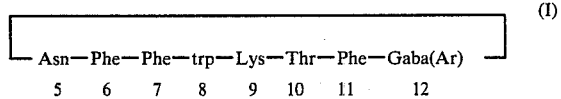

in which
trp represents L-Trp or D-Trp, in which the benzene ring may be substituted by a halogen atom, and
Gaba(Ar) represents the residue of a γ-aminobutyric acid substituted by a cyclic hydrocarbyl radical, and their acid addition salts and complexes are distinguished by a strong inhibition of the insulin and glucagon secretion of the pancreas and are therefore therapeutically acceptable, preferably in the form of pharmaceutical preparations, in similar indications to those of somatostatin, especially as anti-diabetics. The compounds are manufactured by conventional processes of peptide synthesis, especially by liberation from corresponding protected intermediates after intramolecular cyclization of a corresponding linear octapeptide.

15 Claims, No Drawings

CYCLOPEPTIDES AND PHARMACEUTICAL PREPARATIONS THEREOF AND ALSO PROCESSES FOR THEIR MANUFACTURE

The invention relates to new cyclopeptides of the somatostatin type and processes for the manufacture thereof and also to pharmaceutical preparations containing these compounds and the use of these compounds or preparations for therapeutic purposes.

The invention relates especially to cyclopeptides that have the most essential features of somatostatin, such as the partial sequence of amino acids 5–11 or an equivalent sequence, but that are nevertheless free of sulphur. The somatostatin-analogous cyclopeptides according to the invention include cyclic octapeptides of the formula

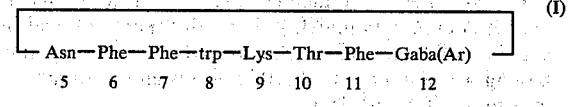
    Asn—Phe—Phe—trp—Lys—Thr—Phe—Gaba(Ar)
     5    6    7    8    9   10   11    12          (I)

in which trp represents L-Trp or D-Trp, in which the benzene ring may be substituted by a halogen atom, and Gaba(Ar) represents the residue of a γ-aminobutyric acid substituted by a cyclic hydrocarbyl radical, and acid addition salts and complexes thereof.

The halogen atom optionally present in the benzene ring of the trp⁸ radical is especially a chlorine or fluorine atom that is preferably in the 5-position; 5-F-D-trp (5-fluoro-D-tryptophyl) and above all D-Trp are especially preferred as trp.

The radical denoted Gaba(Ar) is more precisely defined by the formula

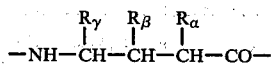

$$\begin{array}{ccc} R_\gamma & R_\beta & R_\alpha \\ | & | & | \\ -NH-CH-CH-CH-CO- \end{array}$$

in which one of the symbols $R_\alpha$, $R_\beta$ and $R_\gamma$ is an unsubstituted or substituted cyclic hydrocarbyl radical Ar and the other two represent hydrogen. The acid corresponding to the radical Gaba(Ar) has the short form H-Gaba(Ar)—OH.

The cyclic hydrocarbyl radical Ar is especially a mono-, di or polycyclic cycloalkyl radical or a corresponding aryl radical containing at least one aromatic ring and having a maximum of 18, preferably a maximum of 12, ring carbon atoms. Of the cycloalkyl radicals, those that are preferred have 3- to 8-membered, and especially 5- and/or 6-membered, rings, such as, for example, cyclopropyl, cyclobutyl, cycloheptyl, cyclooctyl and very especially cyclopentyl and cyclohexyl, also 1-bicyclo[2,2,2]octyl, 2-bicyclo[2,2,2]octyl, 2-bicyclo[2,2,1]heptyl, 1- or 2-adamantyl, and 1- or 2-perhydronaphthyl, i.e. bicyclo[4,4,0]decyl. An aryl radical is especially a naphthyl radical, such as 1- or 2-naphthyl, a corresponding partially hydrogenated naphthyl radical, such as, especially, 1-, 2-, 5- or 6-(1,2,3,4-tetrahydronaphthyl), phenyl, anthryl, fluorenyl or azulenyl. All of these cyclic hydrocarbyl radicals may carry one or more lower aliphatic hydrocarbyl radicals, especially alkyl radicals having a maximum of 4 carbon atoms, for example methyl, ethyl, propyl, isopropyl or butyl, and/or further cyclic, especially monocyclic, hydrocarbyl radicals, such as those defined above, the total number of carbon atoms being a maximum of 18. Examples of such cyclic hydrocarbyl radicals are 4,4-dimethylcyclohexyl, tolyl, such as 2-, 3- or 4-tolyl, and biphenylyl, for example 4-biphenylyl.

The aromatic moiety of the cyclic hydrocarbyl radicals may be substituted by one, two or more identical or different substituents, such as halogen, for example chlorine, bromine, iodine and especially fluorine, lower alkoxy, especially one derived from one of the above-mentioned lower alkyl radicals having a maximum of 4 carbon atoms, including, especially, methoxy, also nitro and amino, especially primary amino, di-lower alkylamino and acylamino, such as lower alkanoylamino, for example acetamino, and also phenoxy radicals that may optionally contain one to three of these substituents. Especially preferred are phenyl radicals substituted by the mentioned substituents, such as 4-fluorophenyl, 4-chlorophenyl, 4-nitrophenyl and especially 3-phenoxyphenyl, and also naphthyl radicals substituted by the mentioned substituents, for example 4-chloro-1-naphthyl.

The radical Ar is found in the α-, γ- or preferably the β-position of the chain of γ-aminobutyric acid; accordingly, especially preferred radicals of the formula Gaba(Ar) are derived from the following butyric acids: 4-amino-3-cyclohexyl-, 4-amino-3-phenyl, 4-amino-3-(4-fluorophenyl)-, 4-amino-3-(4-nitrophenyl)-, 4-amino-3-(4-chloro-1-naphthyl)-, 4-amino-3-(2-naphthyl)- and especially 4-amino-3-(1-naphthyl)- and 4-amino-3-(3-pheoxyphenyl)-butyric acid.

As a result of substitution with the radical Ar, a centre of asymmetry is formed at the corresponding carbon atom of the acid chain which results in the presence of in each case two diastereoisomers of the cyclopeptide according to the invention that may, if desired, be used separately or together, as a diastereoisomeric mixture, for the same purposes. In general, the diastereoisomer termed isomer B is in each case preferred, i.e. that diastereoisomer which is derived from the more hydrophilic diastereoisomer during the countercurrent distribution of corresponding protected intermediates of the formula II (see below).

Especially preferred cyclic octapeptides according to the invention of the formula I are the following: [D-Trp⁸; β-cyclohexyl-Gaba¹²]-cyclosomatostatin(5–12-)octapeptide of the formula

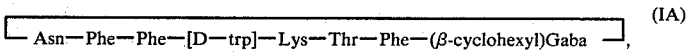

Asn—Phe—Phe—[D—trp]—Lys—Thr—Phe—(β-cyclohexyl)Gaba        (IA)

[D-Trp⁸; β-phenyl-Gaba¹²]-cyclosomatostatin(5–12-)octapeptide of the formula

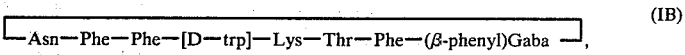

Asn—Phe—Phe—[D—trp]—Lys—Thr—Phe—(β-phenyl)Gaba         (IB)

[5-F-D-Trp⁸; β-(1-naphthyl)-Gaba¹²]-cyclosomatostatin(5–12)-octapeptide of the formula

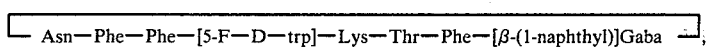
(IC)

and especially [D-Trp⁸; β-(1-naphthyl)-Gaba¹²]-cyclosomatostatin(5–12)-octapeptide of the formula

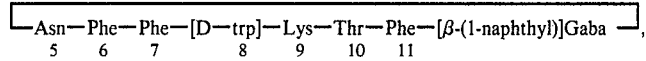
(ID)

and [D-Trp⁸; β-(3-phenoxyphenyl)-Gaba¹²]-cyclosomatostatin(5–12)-octapeptide of the formula

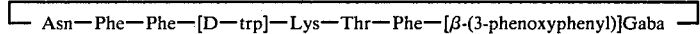
(IE)

Each of these mentioned compounds may be in the form of a diastereoisomeric mixture derived from a racemic [d,l-Gaba(Ar)] radical or in the form of an individual diastereoisomer, for example a diastereoisomer described in the Examples below and characterised by physical data, derived from only one of the optically isomeric forms of the [Gaba(Ar)] radical. In each case, the isomer B of the compounds pointed out above is especially preferred.

All of the somatostatin analogues of the formula I characterised above either in a general manner or as being preferred may alternatively be in the form of acid addition salts or complexes. Suitable acid addition salts are especially physiologically tolerable salts with conventional therapeutically acceptable acids; of the inorganic acids, mention should be made of hydrohalic acids, such as hydrochloric acid, but also of sulphuric acid and phosphoric or pyrophosphoric acid; of the organic acids, mention should be made especially of sulphonic acids, such as benzenesulphonic acid and p-toluenesulphonic acid, or of lower alkanesulphonic acids, such as methanesulphonic acid, also of carboxylic acids, such as acetic acid, lactic acid, palmitic and stearic acid, malic acid, tartaric acid, ascorbic acid and citric acid.

Complexes should be understood as being compounds the structures of which have not yet been fully clarified and that are formed when certain inorganic or organic substances are added to peptides and that impart to these a prolonged action. Such substances are described, for example, for ACTH and other adrenocorticotropically active peptides. Those that should be mentioned are, for example, inorganic compounds that are derived from metals, such as calcium, magnesium, aluminium, cobalt and especially zinc, especially sparingly soluble salts, such as phosphates, pyrophosphates and polyphosphates, as well as hydroxides of these metals, also alkali metal polyphosphates, for example Calgon N ®, Calgon 322 ® or Calgon 188 ®. Organic substances that prolong action are, for example, non-antigenic types of gelatin, for example polyoxygelatin, polyvinylpyrrolidone and carboxymethylcellulose, also sulphonic or phosphoric acid esters of alginic acid, dextran, polyphenols and polyalcohols, especially polyphloretin phosphate and phytic acid, and also polymers and copolymers of basic or, especially, acidic amino acids, for example protamine or polyglutamic acid.

Unless otherwise indicated, the short forms of the amino acid residues refer to radicals of the α-amino acids of the L-series that occur naturally.

Unless otherwise indicated, the term "lower", wherever it occurs in connection with an organic radical or a compound, indicates such as radical or compound having a maximum of 7 carbon atoms and preferably a maximum of 4 carbon atoms.

The new cyclopeptides according to the invention have a physiological action that is fundamentally similar to the action of somatostatin. They can therefore be used advantageously in similar therapeutic indications to those of somatostatin, for example especially for the treatment of functional disorders in which the secretion of the somatotropic hormone or glucagon is abnormally high, such as in the case of acromegalia or diabetes. Since they also inhibit blood losses in the gastrointestinal tract they can also be used successfully in this area of indication.

As is known, somatostatin, a cyclic tetradecapeptide of the formula

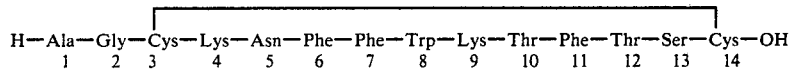

[Science 179, 77 (1973)], inhibits the pituitary-controlled secretion of the somatotropic hormone (somatotropin). It also inhibits the secretory activity of the endocrine pancreas, such as the secretion of insulin and glucagon. In the case of somatostatin itself, these valuable properties cannot be used fully in practice since this compound has too short a duration of action. In addition, it is often advantageous if the active substance exercises its inhibitory effect mainly on one of the two glands while the other gland should be affected as little as possible. (In most cases, the inhibition of the pituitary secretion, i.e. that of the somatotropic hormone release, is less desirable). For this reason, attempts are being made to achieve a dissociation of the inhibitory effects by modifying the basic sequence, especially by omitting individual original amino acids and/or exchanging them for other, often "unnatural", amino acids, and to achieve as long a duration of action as possible. It has been found, for example, that especially advantageous physiological properties of this type occur in cyclopeptides of the type

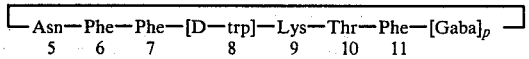

(M)

in which

Gaba represents the residue of γ-aminobutyric acid, and p represents the number 0, 1 or 2, and in other closely related compounds, cf. our European patent application No. 78 100 994.9, published under No. 0 001 295. A typical feature of these compounds is the presence of a straight carbon chain which is intended to simulate the original grouping —CH$_2$—S—S—CH$_2$— in the cystine radical of somatostatin.

Surprisingly it has now been found that by a very unusual modification of this simple unsubstituted chain section, i.e. by the substitution of the γ-amino acid by a cyclic hydrocarbyl radical, the desired activity is not only maintained but increased even further. Thus, compared with somatostatin, the compounds according to the invention of the formula I exhibit both an increased inhibition of insulin and glucagon secretion and also a considerable prolongation of the duration of action. For example, in the determination of insulin and glucagon release using the isolated perfused pancreas of a rat [G. M. Grodsky and R. E. Fanska in "Methods in Enzymology" 39, Part D, page 364; (J. G. Hardman and B. W. O'Malley, editors; Academic Press, New York, 1975)] it was found that the [D-Trp$^8$; β-(1-naphthyl)Gaba$^{12}$]cyclosomatostatin(5–12)-octapeptide (formula ID) has, as a diastereoisomeric mixture, approximately 10 times the inhibitory effect and, as the isolated isomer B, as much as approximately 20 times the inhibitory effect of [D-Trp$^8$; Gaba$^{12}$]-cyclosomatostatin(5–12)-octapeptide (formula M, p=1).

The compounds according to the invention can be manufactured according to methods known per se by cyclising a linear peptide of the formula

H—[II′]-C     (III)

in which

II′ represents a radical corresponding to the formula II defined below in which the amide bond is interrupted between any two adjacent amino acid residues of the peptide ring, and C represents a free hydroxyl group, a hydroxyl group modified by an activating group or represents the hydrazino group —NH—NH$_2$, and splitting off the protecting group(s) in a resulting compound of the formula (II)

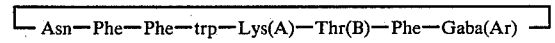

in which

Gaba(Ar) and trp have the meanings given above,

A represents an ε-amino-protecting group or hydrogen, and

B represents a hydroxyl-protecting group or hydrogen, it being possible for only one of the symbols A and B to represent hydrogen.

As ε-amino-protecting groups there may be used any of the amino-protecting groups customarily used in peptide chemistry, as described synoptically in the corresponding reference works, for example in Houben-Weyl: Methoden der organischen Chemie, 4th edition, volume 15/I; E. Wüsch (editor): Synthese von Peptiden. (Georg Thieme Verlag, Stuttgart; 1974). Groups that can be split off by acidolysis are preferred, such as, especially, the tert.-butoxycarbonyl group and analogous groups, for example the tert.-amyloxycarbonyl, isopropoxycarbonyl, diisopropylmethoxycarbonyl, allyloxycarbonyl, cyclopentyloxycarbonyl, cyclohexyloxycarbonyl, d-isobornyloxycarbonyl and adamantyloxycarbonyl groups, and also groups of the aralkyl type, such as benzhydryl and triphenylmethyl (trityl), or certain aralkoxycarbonyl groups of the 2-(p-biphenylyl)-2-propoxycarbonyl type that are described in Swiss Patent Specification No. 509 266.

It is, however, also possible to use amino-protecting groups that can be split off by reduction or by means of bases, for example especially the benzyloxycarbonyl group and benzyloxycarbonyl groups that are substituted in the aromatic moiety by halogen atoms, nitro groups, lower alkoxy groups and/or lower alkyl radicals, such as the p-chloro- and p-bromobenzyloxycarbonyl, p-nitrobenzyloxycarbonyl, p-methoxybenzyloxycarbonyl and p-tolyloxycarbonyl groups, or alternatively the isonicotinyloxycarbonyl group, also acyl groups, such as p-toluenesulphonyl, benzenesulphenyl, o-nitrobenzenesulphenyl or also formyl, trifluoroacetyl or phthaloyl.

An especially advantageous ε-amino-protecting group is an ethoxycarbonyl group that carries in the β-position a silyl group substituted by 3 hydrocarbon radicals, such as a triphenylsilyl, a dimethylbutylsilyl or especially a trimethylsilyl group. A β-(trihydrocarbylsilyl)-ethoxycarbonyl group of this type, such as a β-(tri-lower alkylsilyl)-ethoxycarbonyl group, for example especially the β-(trimethylsilyl)-ethoxycarbonyl group, forms together with the ε-amino group to be protected a corresponding β-trihydrocarbylsilylethoxycarbonylamino group (for example the β-trimethylsilylethoxycarbonylamino group) that is stable under the conditions of acidic hydrolysis and of hydrogenolysis but can be split off by the action of fluoride ions under quite specific, very mild conditions. In this respect it behaves analogously to the β-silylethyl ester group described below as a carboxyl-protecting group. (This similarity must be given particular consideration when synthesising; except for isolated cases, the use of one of these protecting groups precludes the simultaneous use of the other protecting group). Further details are given hereinafter in the description of the protection of the carboxyl group by a β-silylethyl ester.

There may be used as hydroxyl-protecting groups any of the groups conventionally used in peptide chemistry for this purpose, cf. the work cited above (Houben-Weyl). Groups that can be split off by acidolysis, such as 2-tetrahydropyranyl and very especially tert.-butyl, are preferred. It is, however, also possible to use hydroxylprotecting groups that can be split off by reduction or by means of bases, for example benzyl groups that may be substituted in the aromatic moiety by halogen, nitro and/or lower alkoxy, or lower alkanoyl radicals, such as acetyl, or aroyl radicals, such as benzoyl.

The protecting groups A and B are preferably so chosen that they can be split off under similar conditions; especially preferred are the groups that can be split off by acidolysis which have already been pointed out. Both protecting groups can then be split off advantageously in a single operation; it is, however, also possible to use groups of different types and to split off each one individually.

A functional group represented by the symbol C supplements the carbonyl group of the C-terminal amino acid residue and forms together with that group a free carboxyl group, an activated ester group or the carbazolyl group, as the case may be.

The activating group by which the hydroxyl group is modified is especially one that forms the activated ester of N-hydroxysuccinimide, 1-hydroxybenzotriazole, N,N'-dicyclohexylisourea, 2,4,5-trichlorophenol, 2-nitrophenol, 4-nitrophenol, pentachlorophenol or pentafluorophenol but may also be a different activating group of this type known from peptide chemistry, cf. Houben-Weyl, volume 15/II.

Of the linear peptides of the formula III, those in which the radical Gaba(Ar) represents a terminal amino acid in the radical [II'] are preferred. These preferred starting materials are characterized by the formulae

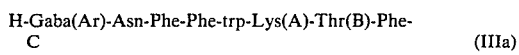
(IIIa)

and especially

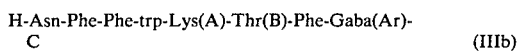
(IIIb)

in which A, B, C, trp and Gaba(Ar) have the meanings given above. Very especially preferred are compounds of the formulae IIIa and IIIb in which A represents an ε-amino-protecting group, especially an ε-amino-protecting group that can be split off by acidolysis, B represents a hydroxyl-protecting group, especially a hydroxyl-protecting group that can be split off by acidolysis, and C represents a free hydroxyl group.

The cyclisation according to the invention of the linear peptide of the formula III is carried out in a manner known per se by means of conventional coupling methods used for the formation of the amide bond, the peptide starting materials, however, being used in a very low concentration in order to influence the course of the coupling operation in favour of intramolecular cyclisation at the expense of intermolecular polycondensation.

The linear peptides are advantageously used in an approximately $1.10^{-4}$— to approximately $1.10^{-2}$—molar concentration, preferably an approximately $1.10^{-3}$—molar concentration, which corresponds to a weight/volume concentration of approximately 0.01 to 1.0%, preferably 0.1%. The reaction mixture can be correspondingly diluted from the start or this dilution can be produced continuously by the slow dropwise addition of the starting material, and optionally the other reagents, to the reaction mixture.

Cyclisation is preferably carried out, at a starting concentration indicated above, by (a) treating a starting material of the formula III, in which C represents a free hydroxyl group and in which both the ε-amino group of the lysine radical and the hydroxyl group of the threonine radical are protected, with a carbodiimide, optionally in the presence of an active ester-forming component, or (b) reacting with an organic base a starting material of the formula III, in which C represents a hydroxyl group modified to form the activated ester and the terminal amino group is present in protonated form, at least the ε-amino group of the lysine radical being protected, or (c) first treating a starting material of the formula III, in which C represents the group —NH—NH₂ and at least the ε-amino group of the lysine radical is protected, with nitrous acid or a lower alkyl ester thereof under acidic conditions and then cyclising with excess organic base at an above-mentioned low concentration.

The cyclisation is carried out in suitable solvents, for example dioxan, tetrahydrofuran, acetonitrile, pyridine, dimethylformamide, dimethylacetamide, dimethylsulphoxide, N-methylpyrrolidone, hexamethylphosphoric acid triamide, and also ethyl acetate, chloroform and methylene chloride, and mixtures thereof.

In process variant (a) the cyclisation is brought about by a carbodiimide, preferably N,N'-dicyclohexylcarbodiimide, that is advantageously used in excess; it is to be assumed that the starting material of the formula III having a free carboxyl group is converted primarily into an activated ester of dicyclohexylisourea (or an analogous isourea) and this active ester formed in situ is immediately subjected to further reaction. The intermediate formation of an active ester can doubtless be attributed to the addition of an active ester-forming component as an auxiliary reagent; for this purpose, active ester-forming components customary in peptide chemistry may be used, such as, especially, 2,4,5-trichlorophenol, 2- or 4-nitrophenol, pentachlorophenol and pentafluorophenol, but above all N-hydroxy compounds, among which N-hydroxysuccinimide, N-hydroxypiperidine and above all 1-hydroxybenzotriazole are especially advantageous. In the case of this variant, the operating temperature is generally 0°–70°, preferably 35°–55°.

In the case of variant (b) which is carried out with ready-prepared active esters, especially those already pointed out, cyclisation takes place spontaneously as soon as the terminal amino group is deprotonated by the base. The bases used are preferably quaternary or especially tertiary amines, for example triethylamine of N-ethylmorpholine. The operation is preferably carried out at 10°–30°, especially at room temperature.

In the case of variant (c), the first phase, i.e. the formation of the acid azide by treating with nitrous acid or an ester thereof, may advantageously be carried out at a considerably higher concentration of the starting materials than in the case of the subsequent cyclisation. The operation is advantageously carried out with approximately one equivalent of a lower alkyl nitrite, such as ethyl nitrite, isoamyl nitrite and especially tert.-butyl nitrite, in a hydrochloric acid medium at temperatures of approximately −30° to approximately −5°, preferably approximately −20°; a slight excess of nitrite is permissible. The solution of the azide formed is then, after the necessary dilution, rendered basic at a temperature of approximately 0° to approximately 35° by means of excess organic base, for example one of those mentioned above, and thereby made to cyclise spontaneously as in the case of process variant (b).

If, according to the invention, a racemic γ-aminobutyric acid H-Gaba(Ar)—OH or a derivative thereof is used as the starting material, then, by combination with an otherwise sterically uniform partial sequence 5-11, a diastereoisomeric pair is obtained. This pair can be separated into individual diastereoisomers by conventional physical methods of separation, for example by fractional precipitation or crystallisation, various chromatographic techniques, such as adsorption and partition chromatography, gel filtration and ion exchange separation, or especially by partitioning between two possible solvent systems, especially by countercurrent distribution (Craig process). Separation according to the last-mentioned method takes place especially advantageously when the compounds are already cyclised, i.e. in the case of the end products of the formula I and especially in the case of their cyclic antecedents of the formula II. (The less hydrophilic diastereoisomer isolated in the course of this operation is designated isomer A and the more hydrophilic diastereoisomer is designated isomer B). The solvent systems suitable for this separation are those generally used in peptide chemistry and in most cases consist of a two-phase combination of chlorinated hydrocarbons, lower alcohols and water that is especially so chosen that both phases are present in approximately equal volumes. These systems are closely related to those used in thin layer chromatography and may be derived from these (cf. also the examples of carrying out the process).

Protecting groups in II are split off in a manner known per se; acid hydrolysis (acidolysis) is carried out, for example, by means of trifluoroacetic acid, hydrochloric acid or hydrofluoric acid or, in the case of acid-sensitive protecting groups, alternatively by means of a lower aliphatic carboxylic acid, such as formic acid and/or acetic acid, in the presence of water and optionally of a polyhalogenated lower alkanol or lower alkanone, such as 1,1,1,3,3,3-hexafluoropropan-2-ol or hexafluoroacetone. The groups that can be split off by reduction, especially those that contain benzyl radicals, are preferably removed by hydrogenolysis, for example by hydrogenation with palladium catalysis. The isonicotinyloxycarbonyl group is preferably split off by zinc reduction.

The end products according to the invention are obtained as bases or as acid addition salts depending on the type of isolation; these may subsequently be interconverted in a manner known per se.

The above-mentioned complexes are also formed according to known methods or methods equivalent to these.

Complexes with inorganic substances, such as sparingly soluble metal compounds, such as aluminium or zinc compounds, are preferably manufactured in a manner analogous to that known for ACTH, for example by reacting with a soluble salt of the metal concerned, for example zinc chloride or zinc sulphate, and precipitating with an alkali metal phosphate and/or hydroxide. Complexes with organic compounds, such as polyoxygelatin, carboxymethylcellulose, polyvinylpyrrolidone, polyphloretin phosphate, polyglutamic acid etc., are obtained by mixing these substances with the peptide in aqueous solution. In the same manner, it is also possible to manufacture insoluble compounds using alkali metal polyphosphates.

The compounds of the above-characterised formula II are new and also belong to the subject of the invention.

The linear peptides of the formula III are also new and, together with their processes of manufacture, also belong to the subject of the present invention. They are obtained according to methods known per se by condensing with one another, in any time sequence, the amino acids or smaller peptide units necessary for their synthesis, with the formation of CONH bonds, it being possible to protect intermediately any functional groups not participating in the reaction.

The linear peptides of the formulae IIIa and IIIb pointed out above as being preferred are obtainable especially from intermediates the manufacture of which has been described in detail in connection with the synthesis of other somatostatin analogues in our above-mentioned European Patent Application, publication No. 0 001 295. The intermediates characterised in this Application already have the preferred (D-Trp)$^8$-somatostatin(5–11) sequence in a suitably protected form and can be condensed directly with suitable derivatives of a substituted γ-aminobutyric acid of the formula H—Gaba(Ar)—OH. For their part, the last-mentioned starting materials are known or can be obtained according to known general processes.

In the manufacture of the linear peptides of the formula III, and also of their intermediates in general, suitable protecting groups for the terminal α-amino and carboxyl groups are especially the protecting groups that are customarily used in the synthesis of long-chained peptides and that can be split off readily and selectively, for example by solvolysis or reduction.

Examples of α-amino-protecting groups are: optionally substituted, for example by halogen, nitro, lower alkyl or lower alkoxy, di- or triaryl-lower alkyl groups, such as diphenylmethyl or triphenylmethyl groups, for example benzhydryl, trityl, di-(p-methoxy)-benzhydryl, or especially groups that are derived from carbonic acid and that can be split off by hydrogenolysis, such as benzyloxycarbonyl groups optionally substituted in the aromatic radical by halogen atoms, nitro groups, lower alkyl or lower alkoxy groups, for example benzyloxycarbonyl (i.e. carbobenzoxy), p-bromo- or p-chlorobenzyloxycarbonyl, p-nitrobenzyloxycarbonyl, p-methoxybenzyloxycarbonyl; also 2-(p-biphenylyl)-2-propoxycarbonyl and similar aryloxycarbonyl groups described in Swiss Patent Specification No. 509 266. It must be ensured that the α-amino-protecting group can be split off selectively while the optionally present ε-amino-protecting group of the lysine radical is retained. It is, moreover, also advantageous if, during the splitting off of the α-amino-protecting group, an optionally present carboxyl-or hydroxyl-protecting group also remains undamaged.

Carboxyl groups are protected, for example, by the formation of hydrazides or by esterification. Suitable for esterification are, for example, lower optionally substituted alkanols, such as methanol, ethanol, cyanomethyl alcohol, 2,2,2-trichloroethanol, benzoylmethyl alcohol and especially tert.-butyl alcohol, or alternatively an optionally substituted benzyl alcohol. An especially advantageous category of substituted alkanols is ethyl alcohols that carry in the β-position a tri-substituted silyl group, such as a triphenylsilyl, a dimethylbutylsilyl or especially a trimethylsilyl group. As described, for example, in Belgian Patent Specification No. 851,576, these alcohols are especially suitable for protecting the carboxyl groups because, although the corresponding β-silylethyl esters, for example β-(trimethylsilyl)-ethyl ester, have the stability of conventional alkyl esters, they can be split off selectively under mild conditions by the action of fluoride ions while all the other protecting groups are retained.

Suitable for the formation of activated esters, such as, for example, in the compounds of the formula III, are, for example, phenols and thiophenols optionally substituted by electron-attracting substituents, such as phenol, thiophenol, thiocresol, p-nitrothiophenol, 2,4,5- and 2,4,6-trichlorophenol, pentachlorophenol, pentafluorophenol, o- and p-nitrophenol, 2,4-dinitrophenol, and p-cyanophenol, and also, for example, N-hydroxysuccinimide, N-hydroxyphthalimide and N-hydroxypiperidine.

The hydroxyl group of the threonine radical can be protected by esterification or etherification, as already indicated above, but it may alternatively remain free.

These protecting groups can be split off in known manner. For example, the benzyloxycarbonyl group can be split off by hydrogenolysis; the N-trityl group by mineral acids, such as hydrohalic acids, for example hydrofluoric acid or preferably hydrochloric acid, or by organic acids, such as formic acid, acetic acid, chloroacetic acid or trifluoroacetic acid, in aqueous or absolute trifluoroethanol as the solvent (cf. German Offenlegungsschrift DT No. 2 346 147), or by aqueous acetic acid; the tert.-butoxycarbonyl group by trifluoroacetic acid or hydrochloric acid; and the 2-(p-biphenylyl)-isopropoxycarbonyl group by aqueous acetic acid or, for example, by a mixture of glacial acetic acid, formic acid, (82.8% strength) and water (7:1:2) or in accordance with the process indicated in DT No. 2 346 147.

The $\beta$-silylethyl ester groups are preferably split off by reagents yielding fluoride ions, for example fluorides of quaternary organic bases, such as tetraethylammonium fluoride. However, they can also be split off, like the conventional alkyl esters, by alkaline hydrolysis, for example by means of alkali metal hydroxides, carbonates or bicarbonates, or they can be converted by hydrazinolysis, for example by means of hydrazine hydrate, into the corresponding carbazoyl groups. Acidolysis is preferably used to split off tert.-butyl esters and hydrogenolysis for benzyl esters.

The condensation of the amino acid units and/or peptide units that must be effected for the manufacture of the linear peptides of the formula III is carried out in a manner known per se preferably by linking an amino acid or peptide having a protected α-amino group and an optionally activated terminal carboxyl group (=active component) to an amino acid or peptide having a free α-amino group and a free or protected, for example esterified, terminal carboxyl group (=passive component), liberating the terminal amino group in the product formed and reacting this peptide, containing a free α-amino group and an optionally protected terminal carboxyl group, with a further active component, i.e. an amino acid or peptide having an activated terminal carboxyl group and a free α-amino group, etc. The carboxyl group can be activated, for example, by converting into an acid azide, anhydride, imidazolide, isoxazolide or an activated ester, such as one of those mentioned hereinbefore, or by reacting with a carbodiimide, such as N,N'-dicyclohexylcarbodiimide, optionally with the addition of N-hydroxysuccinimide or an unsubstituted or, for example, a halogen-, methyl- or methoxy-substituted 1-hydroxybenzotriazole or 4-hydroxybenzo-1,2,3-triazin-3-oxide (inter alia cf. DT No. 1 917 690, DT No. 1 937 656, DT No. 2 202 613), or by reacting with N,N'-carbonyldiimidazole. The most usual coupling method is the carbodiimide method, also the azide method, the activated esters method and the anhydride method, the Merrifield method and the method using N-carboxyanhydride or N-thiocarboxyanhydrides.

In an especially preferred method of manufacturing the linear peptides of the formula III, the coupling method used is the carbodiimide method with N,N'-dicyclohexylcarbodiimide in the presence of 1-hydroxybenzotriazole. The terminal carboxyl group is protected in the form of the $\beta$-(trimethylsilyl)-ethyl ester and the α-amino group of the active component is protected by the benzyloxycarbonyl group which is split off by hydrogenolysis after each coupling step. In order to protect the $\epsilon$-amino group of the lysine radical, acylation with the tert.-butoxycarbonyl group is used and to protect the hydroxyl group of the threonine radical, etherification with the tert.-butyl group is used. These two protecting groups may, if desired, be split off finally in one step by acid hydrolysis, for example by means of trifluoroacetic acid, hydrochloric acid or hydrofluoric acid.

Depending on the method used, the compounds are obtained in the form of bases or their salts. The bases can be obtained from the salts in a manner known per se and, in turn, therapeutically acceptable acid addition salts can be obtained from the bases by reacting with acids, for example with those that form the above-mentioned salts.

Owing to the close relationship between the new compounds in free form and in the form of their salts, hereinbefore and hereinafter the free compounds shall also optionally include the salts thereof and the salts shall also optionally include the free compounds, where appropriate according to meaning and purpose.

The invention also relates to those embodiments of the process in which a compound obtainable as an intermediate at any process stage is used as the starting material and the remaining process steps are carried out, or in which a starting material is formed under the reaction conditions or is used in the form of a derivative thereof, optionally a salt.

In the process of the present invention, the starting materials used are preferably those that result in the compounds described initially as especially valuable.

The present invention also relates to pharmaceutical preparations that contain compounds of the formula I or pharmaceutically acceptable salts thereof. These pharmaceutical preparations may be used especially in the abovementioned indications if they are administered intraperitoneally, such as intravenously, intramuscularly or subcutaneously, or also intranasally. The necessary dose depends on the particular disorder to be treated, its severity and the duration of therapy. The number and quantity of the individual doses and also the administration scheme can best be determined on the basis of an individual examination of the patient concerned. The method of determining these factors is known to the man skilled in the art. As a rule, however, in the case of injection, a therapeutically active quantity of a compound of this type lies in the dosage range of approximately 0.001 to approximately 0.2 mg/kg body weight. The range of approximately 0.0015 to approximately 0.15 mg/kg body weight is preferred and administration is by intravenous infusion or subcutaneous injection. Accordingly, pharmaceutical preparations for parenteral administration in single-dose form contain per dose, depending on the type of medication, approximately 0.08 to approximately 15 mg of one of the compounds according to the invention. Apart from the active substance, they usually also contain a buffer, for example a phosphate buffer, that is to maintain the pH between approximately 3.5 and 7, and also sodium chloride, mannitol or sorbitol for adjusting the isotonia. They may be in freeze-dried or dissolved form and solutions may advantageously contain an antibacterially active preservative, for example 0.2–0.3% of 4-hydroxybenzoic acid methyl ester or ethyl ester. If the active substance in such preparations is to be in the form of a complex having a prolonged duration of action then it may be formed directly by adding the complex-forming components to an injection solution that is prepared, for example, according to the above-mentioned methods. A suitable additive is, for example, 0.1–1.0% by weight of a zinc(II) salt (for example sulphate) in conjunction with 0.5–5.0% by weight of protamine (for example as a sulphate), calculated on the total volume of the injection solution; this preparation is in the form of a solution having a pH of 3.5 to approximately 6.5 or in the form of a suspension having a pH of approximately 7.5 to 8.0.

A preparation for intranasal administration may be an aqueous solution or gel, an oily solution or suspension, or a fat-containing salve. A preparation in the form of an aqueous solution is obtained, for example, by dissolving the active substance of the formula I, or a therapeutically acceptable acid addition salt thereof, in an aqueous buffer solution having a pH of up to 7.2 and adding a substance producing isotonia. A polymeric adhesive, for example polyvinylpyrrolidone, and/or a preservative are advantageously added to the aqueous solution. The individual dose is approximately 0.08 to approximately 15 mg, preferably 0.25 to 10 mg, that are contained in approximately 0.05 ml of a solution or 0.05 g of a gel.

An oily form of medication for intranasal administration is obtained, for example, by suspending a peptide of the formula I, or a therapeutically acceptable acid addition salt thereof, in an oil, optionally with the addition of swelling agents, such as aluminium stearate, and/or interfacially active agents (surfactants), the HLB value ("hydrophilic-lipophilic balance") of which is less than 10, such as fatty acid mono-esters of polyhydric alcohols, for example glycerine monostearate, sorbitan monolaurate, sorbitan monostearate or sorbitan monoleate. A fat-containing salve is obtained, for example, by suspending the active substance according to the invention in a spreadable fat base, optionally with the addition of a surfactant having a HLB value of less than 10. An emulsion salve is obtained by triturating an aqueous solution of the peptide active substance in a soft, spreadable fat base with the addition of a surfactant the HLB value of which is less than 10. All these intranasal forms of medication may also contain preservatives. The individual doses are approximately 0.08 to approximately 15 mg, preferably 0.25 to 10 mg, contained in approximately 0.05 to approximately 0.1 g of the base substance.

Also suitable for intranasal administration are inhalation or insufflation preparations, such as insufflation capsules that permit the active substance to be insufflated in the form of a powder with respiratory air, or aerosols or sprays that can disperse the pharmacological active substance in the form of a powder or in the form of drops of a solution or suspension. Preparations having powder-dispersing properties generally contain adjuncts in addition to the active substance: insufflation capsules contain, for example, solid carriers, such as lactose; aerosol or spray preparations contain, for example, a liquid propellant having a boiling point of below room temperature and, if desired, other carriers, such as liquid or solid non-ionic or anionic surfactants and/or solid diluents. Preparations in which the pharmacological active substance is in solution contain, in addition to this, a suitable propellant and also, if necessary, an additional solvent and/or a stabiliser. Instead of the propellant, it is also possible to use compressed air that is produced when required by means of a suitable compressing and releasing device.

The invention also relates to the use of the new compounds of the formula I and therapeutically acceptable acid addition salts thereof as pharmacologically active compounds, especially in indications usual for somatostatin, preferably in the form of pharmaceutical preparations. The daily dose administered to a warm-blooded animal weighing approximately 70 kg is from approximately 0.1 to approximately 120 mg.

The invention is illustrated in the following Examples but is not limited by these. Temperatures are given in degrees Centigrade; the conventional short forms, for example those compiled in "Synthese von Peptiden" (editor; E. Wünsch), volume XV of "Methoden der org. Chemie" (Houben-Weyl) (1974; G. Thieme, Stuttgart) are used as abbreviations, for example for denoting amino acids, peptides, protecting groups, etc. The following abbreviations, in particular, are used:

Boc—tert.-butoxycarbonyl
But—tert.-butyl (as ether-forming group)
DCC—N,N'-dicyclohexylurea
DCCI—N,N'-dicyclohexylcarbodiimide
Gaba—4-aminobutyric acid residue —NH—(CH$_2$)$_3$—CO—
OBzl—benzyloxy (as ester-forming group)
Z—benzyloxycarbonyl (carbobenzoxy)
CD—circular dichroism
ORD—optical rotation dispersion
TLC—thin layer chromatography.

In TLC, unless otherwise indicated, silica gel is used as the adsorbent and the following systems are used as eluants:

| System | | |
|---|---|---|
| 52 : | n-butanol/acetic acid/water (75:7.5:21) | |
| 101 : | n-butanol/pyridine/acetic acid/water (38:24:8:30) | |
| 111B: | n-butanol/pyridine/25% aqueous ammonia/water (40:24:6:30) | |
| 112A: | n-butanol/pyridine/formic acid/water (42:24:4:20) | |
| 157A: | chloroform/methanol/water/acetic acid (90:10:1:0.5) | |
| 157C: | chloroform/methanol/water/acetic acid (75:27:5:0.5) | |
| 157F: | chloroform/methanol/water/acetic acid (70:40:9:0.5). | |

EXAMPLE 1A

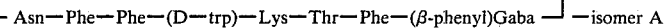

Asn—Phe—Phe—(D—trp)—Lys—Thr—Phe—(β-phenyl)Gaba  —isomer A 160 mg of protected octapeptide of the formula

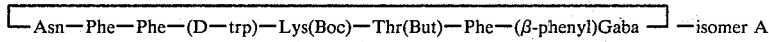

Asn—Phe—Phe—(D—trp)—Lys(Boc)—Thr(But)—Phe—(β-phenyl)Gaba  —isomer A are dissolved at 5° under N₂ in 1.5 ml of a mixture of 89% by volume of trifluoroacetic acid, 10% by volume of water and 1% by volume of thioglycolic acid; the solution is immediately heated to 25° and after 50 minutes at this temperature is precipitated with 5 ml of peroxide-free ether. The resulting crude trifluoroacetate of the end product is filtered off, dried in vacuo, dissolved in 5 ml of 1 N acetic acid and filtered through 15 ml of an anion exchanger, for example AG ® 1-X8 (a product of Bio-Rad Laboratories, Richmond, Calif., USA), in acetate form; the eluate is lyophilised.

The resulting title compound is uniform in three systems according to thin layer chromatography.

| TLC(cellulose, Merck): system | 101 : R$_f$ 0.66 |
|---|---|
| | 111B: R$_f$ 0.48 |
| | 112A: R$_f$ 0.60 |
| CD(in water):λ(nm)/mol. ellipt.: 235/−5800(min); 223/+6600(max). | |

In an analogous manner, the following end products of the formula

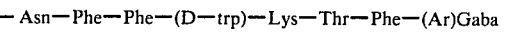

are also obtained from corresponding protected octapeptides:

(Ar)Gaba=β-(2-naphthyl)Gaba—isomer A
TLC: system 157C: R$_f$ 0.27;
(Ar)Gaba=β-(2-naphthyl)Gaba—isomer B
TLC: system 157C: R$_f$ 0.27;
(Ar)Gaba=β-(4-fluorophenyl)Gaba—isomer B
TLC: system 157C: R$_f$ 0.29.

EXAMPLE 18B

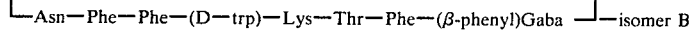 —isomer B 189 mg of protected octapeptide of the formula

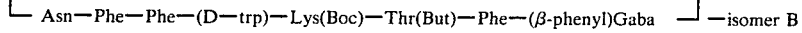 —isomer B are dissolved at 5° under N₂ in 1.9 ml of a mixture of 89% by volume of trifluoroacetic acid, 10% by volume of water and 1% by volume of thioglycolic acid; the solution is immediately heated to 25° and after 50 minutes at this temperature is precipitated with 5 ml of peroxide-free ether. The resulting crude trifluoroacetate of the end product is filtered off, dried in vacuo, dissolved in 5 ml of 1 N acetic acid and filtered through 15 ml of an anion exchanger, for example AG ® 1-X8 (a product of Bio-Rad Laboratories, Richmond, Calif., USA), in acetate form. The eluate is concentrated by evaporation in vacuo and the residue is subjected to countercurrent distribution over 270 stages in the system n-butanol/acetic acid/water (2400:600:3000). The phases contained in units 229 to 250 (K=6.7) are collected, concentrated by evaporation in vacuo and lyophilised from tert.-butanol/water (1:1).

The resulting title compound is uniform in three systems according to thin layer chromatography.

| TLC (cellulose, Merck): | system 101 : | R$_f$ 0.64 |
|---|---|---|
| | 111B : | R$_f$ 0.48 |
| | 112A : | R$_f$ 0.58 |
| CD: (in water): λ (nm)/mol. ellipt.: 235/−3700(min); 220/+35000(max). | | |

The peptide starting materials of Examples 1A and 1B are obtained in the following manner:

STAGE 1.1 d,l-H-(β-phenyl)Gaba-OBzl-p-toluenesulphonate

A mixture of 1.10 g of d,l-4-amino-3-phenylbutyric acid and 1.17 g of p-toluenesulphonic acid monohydrate in 3.2 ml of benzyl alcohol and 50 ml of benzene is distilled slowly under normal pressure until in the course of 3 hours a total of 40 ml of a fraction, b.p. 70°–90°, is collected. The clear reaction solution is concentrated to 3 ml in a water-jet vacuum and then in a high vacuum at approximately 60°. The precipitated crystal mass is stirred with 15 ml of ether and the crystals are filtered off and washed with 10 ml of ether. For further purification, this material is stirred with 10 ml of ether at room temperature for one hour, filtered off, washed with ether and dried in vacuo, m.p. 145°–8°. TLC: [chloroform/methanol/water (14:6:1)] R$_f$ 0.40 [chloroform/methanol (85:15)] R$_f$ 0.17.

The following are obtained in an analogous manner:
(a) from d,l-4-amino-3-(2-naphthyl)-butyric acid, the d,l-H-[β-(2-naphthyl)]Gaba-OBzl-p-toluenesulphonate,
TLC: system 157C: R$_f$ 0.48; and
(b) from d,l-4-amino-3-(4-fluorophenyl)-butyric acid, the d,l-H-[β-(4-fluorophenyl)]Gaba-OBzl-p-toluenesulphonate,
TLC: system 157: R$_f$ 0.45.

STAGE 1.2

Z-Asn-Phe-Phe-(D-trp)-Lys(Boc)-Thr(But)-Phe-[d,l-(β-phenyl)Gaba]-OBzl 0.048 ml of N-methylmorpholine, 58 mg of N-hydroxybenzotriazole and 104 mg of DCCI are added to a mixture of 500 mg of Z-Asn-Phe-Phe-(D-trp)-Lys(Boc)-Thr(But)-Phe-OH (see the above-mentioned European patent application, Example 1, stage 1.7) and 189 mg of d,l-4-amino-3-phenylbutyric acid benzyl ester p-toluenesulphonate (stage 1.1) in 2 ml of dimethylformamide and left to stand for 20 hours at room temperature. For working up, the precipitated DCC is centrifuged off, 15 ml of water are added to the supernatant liquid and filtration is effected. For further purification, the solid substance obtained is stirred with 3 ml of ethanol for 10 minutes, the suspension is cooled to 0° and the pure product is filtered off and dried in vacuo. TLC: [chloroform/methanol (85:15)] R$_f$ 0.70.

In an analogous manner, the following are obtained from corresponding compounds of stage 1.1:
(a) Z-Asn-Phe-Phe-(D-trp)-Lys(Boc)-Thr(But)-Phe-{d,l-[β-(2-naphthyl)]Gaba}-OBzl, TLC: system 157A: R$_f$ 0.65; and (b) Z-Asn-Phe-Phe-(D-trp)-Lys(Boc)-Thr(But)-Phe-{d,l-[β-(4-fluorophenyl)]Gaba}-OBzl, TLC: system 157A: R_f 0.64.

STAGE 1.3

H-Asn-Phe-Phe-(D-trp)-Lys(Boc)-Thr(But)-Phe-[d,l-(β-phenyl)Gaba]-OH

After the addition of 50 mg of palladium-on-carbon (10%), a solution of 453 mg of Z-Asn-Phe-Phe-(D-trp)-Lys(Boc)-Thr(But)-Phe-[d,l-(β-phenyl)Gaba]-OBzl (stage 1.2) in 20 ml of dimethylformamide is hydrogenated for 3 hours at room temperature under normal pressure. For working up, the solution is concentrated to 2 ml in a high vacuum after filtering off the catalyst and the product is precipitated with 25 ml of peroxide-free ether, filtered off and dried in vacuo. The crude product is subjected to the next stage 1.4 (cyclisation) without further purification.

In an analogous manner, the following are obtained from corresponding compounds of stage 1.2:

(a) H-Asn-Phe-Phe-(D-trp)-Lys(Boc)-Thr(But)-Phe-{d,l-[β-(2-naphthyl)]Gaba}—OH; TLC: system 157C: R_f 0.67; and (b) H-Asn-Phe-Phe-(D-trp)-Lys(Boc)-Thr(But)-Phe-{d,l-[β-(4-fluorophenyl)]Gaba}-OH, TLC: system 157A: R_f 0.06.

STAGE 1.4

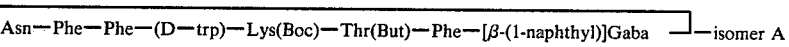

A solution of 386 mg of crude H-Asn-Phe-Phe-(D-trp)-Lys(Boc)-Thr(But)-Phe-[d,l-(β-phenyl)Gaba]-OH (stage 1.3), 400 mg of N-hydroxybenzotriazole and 610 mg of DCCI in 300 ml of dimethylformamide is maintained at 50° for 20 hours. For working up, the solvent is evaporated off in a high vacuum at approximately 30° and the residue is triturated with 15 ml of ethyl acetate. The precipitated dicyclohexylurea is removed by filtration, the filtrate is diluted with ethyl acetate to 50 ml, washed three times with 40 ml of 1 N aqueous oxalic acid each time and then with water until neutral, dried over sodium sulphate and concentrated by evaporation in vacuo. For purifying and separating the diastereoisomers A and B the crude product is subjected to countercurrent distribution over 440 stages in the system methanol/water/chloroform/carbon tetrachloride (2700:675:900:1575 parts by volume). The phases found in units 104 to 155 (K=0.41) contain one of the two diastereoisomers (isomer A) and those found in units 164 to 207 (K=0.70) contain the other (isomer B). The phases of the corresponding units are combined and concentrated by evaporation in vacuo. The residue is dissolved in 20 ml of tert.-butanol and lyophilised whereby, in each case, a diastereoisomer of the above common formula is formed that is uniform according to thin layer chromatography.

TLC: [chloroform/methanol (85:15)] isomer A: R_f 0.65
isomer B: R_f 0.55
[chloroform/methanol/water (14:6:1)]
isomer A: R_f 0.95
isomer B: R_f 0.90.

In an analogous manner, the following are obtained from corresponding compounds of stage 1.3:

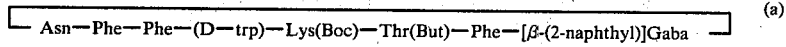 (a)

isomer A: K=0.27; TLC: system 157A: R_f 0.39
isomer B: K=0.51; TLC: system 157A: R_f 0.32, and

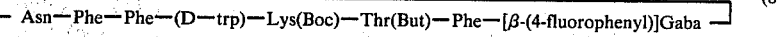 (b)

isomer B: K=0.78; TLC: system 157A: R_f 0.31.

EXAMPLE 2A

Asn—Phe—Phe—(D—trp)—Lys—Thr—Phe—[β-(1-naphthyl)]Gaba ⎯⎯ isomer A 250 mg of protected octapeptide of the formula Asn—Phe—Phe—(D—trp)—Lys(Boc)—Thr(But)—Phe—[β-(1-naphthyl)]Gaba ⎯⎯ isomer A are dissolved at 5° under N_2 in 2.5 ml of a mixture of 89% by volume of trifluoroacetic acid, 10% by volume of water and 1% by volume of thioglycolic acid; the solution is immediately heated to 25° and precipitated with 8 ml of peroxide-free ether after 50 minutes at this temperature. The resulting crude trifluoroacetate of the end product is filtered off, dried in vacuo, dissolved in 5 ml of 1 N acetic acid and filtered through 15 ml of an anion exchanger, for example AG ® 1-X8 (a product of Bio-Rad Laboratories, Richmond, Calif., USA), in acetate form; the eluate is lyophilised.

The resulting title compound is uniform in three systems according to thin layer chromatography.

TLC (cellulose, Merck): system 101 : R_f 0.60
111B : R_f 0.45
112A : R_f 0.58
CD (in 1% aqueous acetic acid): λ (nm)/mol. ellipt.: 226/−8000(min).

EXAMPLE 2B

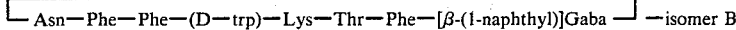 —isomer B 257 mg of protected octapeptide of the formula

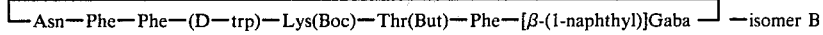 —isomer B are dissolved at 5° under N₂ in 2.5 ml of a mixture of 89% by volume of trifluoroacetic acid, 10% by volume of water and 1% by volume of thioglycolic acid; the solution is immediately heated to 25° and precipitated with 10 ml of peroxide-free ether after 50 minutes at this temperature. The resulting crude trifluoroacetate of the end product is filtered off, dried in vacuo, dissolved in 5 ml of 1 N acetic acid and filtered through 15 ml of anion exchanger, for example AG ® 1-X8 (a product of Bio-Rad Laboratories, Richmond, Calif., USA), in acetate form; the eluate is lyophilised.

The resulting title compound is uniform in three systems according to thin layer chromatography.

TLC (cellulose, Merck): system 101 : $R_f$ 0.57
111B : $R_f$ 0.44
112A : $R_f$ 0.53

CD (in 1% aqueous acetic acid): λ (nm)/mol. ellipt.:
237/+6500(max); 231/−7000(min); 223/+12000(max).

The peptide starting material of Examples 2A and 2B may be obtained as follows:

STAGE 2.1 d,l-H-[β-(1-naphthyl)]Gaba-OBzl-p-toluenesulphonate

A mixture of 1.05 g of d,l-4-amino-3-(1-naphthyl)-butyric acid and 0.871 g of p-toluenesulphonic acid monohydrate in 2.4 ml of benzyl alcohol and 50 ml of benzene is distilled slowly under normal pressure until in the course of 3 hours a total of 40 ml of a fraction, b.p. 70°–90°, is collected. The clear reaction solution is concentrated to 3 ml in a water-jet vacuum and then in a high vacuum at approximately 60°. The precipitated crystal mass is stirred with 15 ml of ether and the crystals are filtered off and washed with 10 ml of ether. For further purification, this material is stirred with 10 ml of ether at room temperature for one hour, filtered off, washed with ether and dried in vacuo, m.p. 152°–4°

TLC: [chloroform/methanol/water (14:6:1) $R_f$ 0.60
[chloroform/methanol (85:15)] $R_f$ 0.28.

STAGE 2.2

Z-Asn-Phe-Phe-(D-trp)-Lys(Boc)-Thr(But)-Phe-[d,l-β-(1-naphthyl)]Gaba-OBzl 0.067 ml of N-methylmorpholine, 81 mg of N-hydroxybenzotriazole and 147 mg of DCCI are added to a mixture of 700 mg of Z-Asn-Phe-Phe-(D-trp)-Lys(Boc)-Thr(But)-Phe-OH (cf. stage 1.2) and 295 mg of d,l-4-amino-3-(1-naphthyl)-butyric acid benzyl ester p-toluenesulphonate (stage 2.1) in 2 ml of dimethylformamide and left to stand for 20 hours at room temperature. For working up, the precipitated DCC is centrifuged off, 20 ml of water are added to the supernatant liquid and filtration is effected. For further purification the solid substance obtained is stirred for 10 minutes with 3 ml of methanol, the suspension is cooled to 0° and the pure product is filtered off and dried in vacuo.

TLC: [chloroform/methanol (85:15)] $R_f$ 0.72
[chloroform/methanol/water (14:6:1)] $R_f$ 0.93.

STAGE 2.3

H-Asn-Phe-Phe-(D-trp)-Lys(Boc)-Thr(But)-Phe-[d,l-β-(1-naphthyl)]Gaba-OH

After the addition of 80 mg of palladium-on-carbon (10%), a solution of 794 mg of Z-Asn-Phe-Phe-(D-trp)-Lys(Boc)-Thr(But)-Phe-[d,l-β-(1-naphthyl)]Gaba-OBzl (stage 2.2) in 40 ml of dimethylformamide is hydrogenated for 4 hours at room temperature under normal pressure. For working up, the solution is concentrated to 2 ml in a high vacuum after filtering off the catalyst and the product is precipitated with 40 ml of peroxide-free ether, filtered off and dried in vacuo. The crude product is subjected to the next stage 2.4 (cyclisation) without further purification.

STAGE 2.4

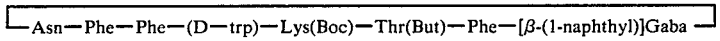

A solution of 678 mg of crude H-Asn-Phe-Phe-(D-trp)-Lys(Boc)-Thr(But)-Phe-[d,l-β-(1-naphthyl)]Gaba-OH (stage 2.3), 676 mg of N-hydroxybenzotriazole and 1030 mg of DCCI in 500 ml of dimethylformamide is maintained at 50° for 20 hours. For working up, the solvent is evaporated off in a high vacuum at approximately 30° and the residue is triturated with 20 ml of ethyl acetate. The precipitated dicyclohexylurea is removed by filtration, the filtrate is diluted with ethyl acetate to 200 ml, washed three times with 50 ml of 1 N aqueous oxalic acid each time and then with water until neutral, dried over sodium sulphate and concentrated by evaporation in vacuo. For purification, the crude product is subjected to countercurrent distribution over 560 stages in the system methanol/water/chloroform/-carbon tetrachloride (2700:675:900:1575 parts by volume). The phases found in units 89 to 143 (K=0.22) contain one of the two diastereoisomers (isomer A) and the phases found in units 152 to 224 (K=0.47) contain the other (isomer B). The phases of the corresponding units are combined and concentrated by evaporation in vacuo. The residue is dissolved in 20 ml of tert.-butanol and lyophilised whereby, in each case, a diastereoisomer of the above common formula is formed that is uniform according to thin layer chromatography.

| TLC: | [chloroform/methanol (85:15)] | isomer A: R$_f$ 0.60; |
|---|---|---|
| | | isomer B: R$_f$ 0.50. |

EXAMPLE 3A 182 mg of protected octapeptide of the formula

└─ Asn—Phe—Phe—(D—trp)—Lys—Thr—Phe—(β-cyclohexyl)Gaba ─┘—isomer A

└─ Asn—Phe—Phe—(D—trp)—Lys(Boc)—Thr(But)—Phe—(β-cyclohexyl)Gaba ─┘—isomer A are dissolved at 5° under N$_2$ in 1.8 ml of a mixture of 89% by volume of trifluoroacetic acid, 10% by volume of water and 1% by volume of thioglycolic acid; the solution is immediately heated to 25° and precipitated with 6 ml of hexane/ether (2:1) after 50 minutes at this temperature. The resulting crude trifluoroacetate of the end product is filtered off, dried in vacuo, dissolved in 5 ml of 1 N acetic acid and filtered through 15 ml of an anion exchanger, for example AG ® 1-X8 (a product of Bio-Rad Laboratories, Richmond, Calif., USA), in acetate form; the eluate is lyophilised.

The resulting title compound is uniform in three systems according to thin layer chromatography.

| TLC: | system 101 : | R$_f$ 0.88 |
|---|---|---|
| | 111B : | R$_f$ 0.50 |
| | 112A : | R$_f$ 0.78. |

EXAMPLE 3B 167 mg of protected octapeptide of the formula

└─ Asn—Phe—Phe—(D—trp)—Lys—Thr—Phe—(β-cyclohexyl)Gaba ─┘—isomer B

└─ Asn—Phe—Phe—(D—trp)—Lys(Boc)—Thr(But)—Phe—(β-cyclohexyl)Gaba ─┘—isomer B are dissolved at 5° under N$_2$ in 1.7 ml of a mixture of 89% by volume of trifluoroacetic acid, 10% by volume of water and 1% by volume of thioglycolic acid; the solution is immediately heated to 25° and precipitated with 6 ml of hexane/ether (2:1) after 50 minutes at this temperature. The resulting crude trifluoroacetate of the end product is filtered off, dried in vacuo, dissolved in 5 ml of 1 N acetic acid and filtered through 15 ml of an anion exchanger, for example AG ® 1-X8 (a product of Bio-Rad Laboratories, Richmond, Calif., U.S.A.), in acetate form; the eluate is lyophilised.

The resulting title compound is uniform in three systems according to thin layer chromatography.

| TLC: System 101 | : | R$_f$ 0.83 |
|---|---|---|
| 111B | : | R$_f$ 0.75 |
| 112A | : | R$_f$ 0.70 |

The peptide starting material of Examples 3A and 3B may be obtained in the following manner:

STAGE 3.1 d,l-H-(β-cyclohexyl)Gaba-OBzl-p-toluenesulphonate

A mixture of 0.50 g of d,l-4-amino-3-cyclohexylbutyric acid hydrochloride and 0.428 g of p-toluenesulphonic acid monohydrate in 1.2 ml of benzyl alcohol and 40 ml of benzene is distilled slowly under normal pressure until in the course of 3 hours a total of 30 ml of a fraction, b.p. 70°–90°, is collected. The clear reaction solution is concentrated to 3 ml in a water-jet vacuum and then in a high vacuum at approximately 60°. The precipitated crystal mass is stirred with 15 ml of ether and the crystals are filtered off and washed with 10 ml of ether. For further purification, this material is stirred with 10 ml of ether at room temperature for one hour, filtered off, washed with ether and dried in vacuo.

| TLC: | [chloroform/methanol/water (14:6:1)] | R$_f$ 0.48 |
|---|---|---|
| | [chloroform/methanol (85:15)] | R$_f$ 0.15. |

STAGE 3.2

Z-Asn-Phe-Phe-(D-trp)-Lys(Boc)-Thr(But)-Phe-(d,l-β-cyclohexyl)Gaba-OBzl 0.111 ml of N-methylmorpholine, 123 mg of N-hydroxybenzotriazole and 223 mg of DCCI are added to a mixture of 1.06 g of Z-Asn-Phe-Phe-(D-trp)-Lys(-Boc)-Thr(But)-Phe-OH (cf. stage 1.2) and 448 mg of d,l-4-amino-3-cyclohexylbutyric acid benzyl ester p-toluenesulphonate (stage 3.1) in 5 ml of dimethylformamide and left to stand for 20 hours at room temperature. For working up, the precipitated DCC is centrifuged off, 20 ml of water are added to the supernatant liquid and filtration is effected. For further purification, the solid substance obtained is stirred with 3 ml of methanol for 10 minutes, the suspension is cooled to 0° and the pure product is filtered off and dried in vacuo.

| TLC: | [chloroform/methanol (85:15)] | R$_f$ 0.80 |
|---|---|---|
| | [chloroform/methanol/water (14:6:1)] | R$_f$ 0.95. |

STAGE 3.3

H-Asn-Phe-Phe-(D-trp)-Lys(Boc)-Thr(But)-Phe-(d,l-β-cyclohexyl)Gaba—OH

After the addition of 100 mg of palladium-on-carbon (10%), a solution of 980 mg of Z-Asn-Phe-Phe-(D-trp)-Lys(Boc)-Thr(But)-Phe-(d,l-β-cyclohexyl)Gaba-OBzl (stage 3.2) in 50 ml of dimethylformamide is hydrogenated for 4 hours at room temperature under normal pressure. For working up, the solution is concentrated to 2 ml in a high vacuum after filtering off the catalyst and the product is precipitated with 40 ml of peroxide-free ether, filtered off and dried in vacuo. The crude product is subjected to the next stage 3.4 (cyclisation) without further purification.

STAGE 3.4

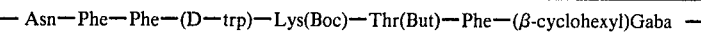
Asn—Phe—Phe—(D—trp)—Lys(Boc)—Thr(But)—Phe—(β-cyclohexyl)Gaba

A solution of 836 mg of crude H-Asn-Phe-Phe-(D-trp)-Lys(Boc)-Thr(But)-Phe-(d,l-β-cyclohexyl)Gaba-OH (stage 3.3), 860 mg of N-hydroxybenzotriazole and 1.31 g of DCCI in 640 ml of dimethylformamide is maintained at 50° for 20 hours. For working up, the solvent is evaporated off in a high vacuum at approximately 30° and the residue is triturated with 20 ml of ethyl acetate. The precipitated dicyclohexylurea is removed by filtration and the filtrate is diluted with ethyl acetate to 200 ml, washed three times with 50 ml of 1 N aqueous oxalic acid each time and then with water until neutral, dried over sodium sulphate and concentrated by evaporation in vacuo. For purification, the crude product is subjected to countercurrent distribution over 400 stages in the system methanol/water/chloroform/-carbon tetrachloride (2700:675:900:1575 parts by volume). The phases found in units 81 to 108 (K=0.30) contain one of the two diastereoisomers (isomer A) and the phases found in units 120 to 147 (K=0.49) contain the other (isomer B). The phases of the corresponding units are combined and concentrated by evaporation in vacuo. The residue is dissolved in 20 ml of tert.-butanol and lyophilised whereby in each case a diastereoisomer of the above common formula is formed that is uniform according to thin layer chromatography.

| TLC: | [chloroform/methanol (85:15)] | isomer A: $R_f 0.51$, |
| | | isomer B: $R_f 0.42$. |

EXAMPLE 4A 280 mg of protected octapeptide of the formula

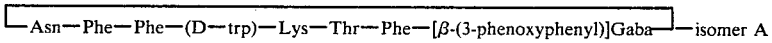
Asn—Phe—Phe—(D—trp)—Lys(Boc)—Thr(But)—Phe—[β-(3-phenoxyphenyl)]Gaba —isomer A are dissolved at 5° under $N_2$ in 2.8 ml of a mixture of 89% by volume of trifluoroacetic acid, 10% by volume of water and 1% by volume of thioglycolic acid; the solution is immediately heated to 25° and precipitated with 25 ml of peroxide-free ether after 50 minutes at this temperature. The resulting crude trifluoroacetate of the end product is filtered off, dried in vacuo, dissolved in 5 ml of 1 N acetic acid and filtered through 15 ml of an anion exchanger, for example AG ® 1-X8 (a product of Bio-Rad Laboratories, Richmond, Calif., USA), in acetate form; the eluate is lyophilised.

The resulting title compound is uniform in three systems according to thin layer chromatography.

| TLC: system 52 | : | $R_f 0.49$ |
| | 111B: | $R_f 0.40$ |
| | 157F: | $R_f 0.53$ |

CD: in 1% aqueous acetic acid: λ/mol. ellipt.
[nm/grad . cm$^2$ . dmol$^{-1}$]: 210/−37430(min); 222/−534(max); 230/−15506(min).

EXAMPLE 4B 268 mg of protected octapeptide of the formula

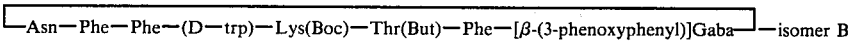
Asn—Phe—Phe—(D—trp)—Lys(Boc)—Thr(But)—Phe—[β-(3-phenoxyphenyl)]Gaba —isomer B are dissolved at 5° under $N_2$ in 2.7 ml of a mixture of 89% by volume of trifluoroacetic acid, 10% by volume of water and 1% by volume of thioglycolic acid; the solution is immediately heated to 25° and precipitated with 30 ml of peroxide-free ether after 50 minutes at this temperature. The resulting crude trifluoroacetate of the end product is filtered off, dried in vacuo, dissolved in 5 ml of 1 N acetic acid and filtered through 15 ml of an anion exchanger, for example AG ® 1-X8 (a product of Bio-Rad Laboratories, Richmond, Calif., USA), in acetate form; the eluate is lyophilised.

The resulting title compound is uniform in three systems according to thin layer chromatography.

| TLC: system 52 | : | $R_f 0.49$ |
| | 111B: | $R_f 0.38$ |
| | 157F: | $R_f 0.52$ |

CD: in 1% aqueous acetic acid: λ/mol. ellipt.
[nm/grad . cm$^2$ . dmol$^{-1}$]: 220/+30354(max); 232.5/−13811(min).

The peptide starting material of Examples 4A and 4B may be obtained in the following manner:

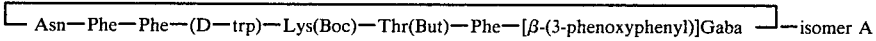
Asn—Phe—Phe—(D—trp)—Lys—Thr—Phe—[β-(3-phenoxyphenyl)]Gaba —isomer A

STAGE 4.1 d,l-H-[β-(3-phenoxyphenyl)]Gaba-OBzl-p-toluenesulphonate

A mixture of 0.500 g of d,l-4-amino-3-(3-phenoxyphenyl)-butyric acid hydrochloride and 0.308 g of p-toluenesulphonic acid monohydrate in 0.85 ml of benzyl alcohol and 70 ml of benzene is distilled slowly under normal pressure until in the course of 3 hours a total of 30 ml of a fraction, b.p. 70°–90°, is collected. The clear reaction solution is concentrated to 3 ml in a water-jet vacuum and then in a high vacuum at approximately 60°. The precipitated crystal mass is stirred with 15 ml of ether and the crystals are filtered off and washed with 10 ml of ether. For further purification, this material is stirred with 10 ml of ether at room temperature for one hour, filtered off, washed with ether and dried in vacuo.

TLC: [chloroform/methanol/water (14:6:1)] $R_f$ 0.61
[chloroform/methanol (85:15)] $R_f$ 0.30.

Stage 4.2

Z-Asn-Phe-Phe-(D-trp)-Lys(Boc)-Thr(But)-Phe-[d,l-β-(3-phenoxyphenyl)]Gaba-OBzl 0.071 ml of N-methylmorpholine, 95 mg of N-hydroxybenzotriazole and 171 mg of DCCI are added to a mixture of 819 mg of Z-Asn-Phe-Phe-(D-trp)-Lys(-Boc)-Thr(But)-Phe—OH (cf. stage 1.2) and 341 mg of d,l-4-amino-3-(3-phenoxyphenyl)-butyric acid benzyl ester p-toluenesulphonate (stage 4.1) in 6 ml of dimethylformamide and left to stand for 20 hours at room temperature. For working up, the precipitated DCC is centrifuged off, 20 ml of water are added to the supernatant liquid and filtration is effected. For further purification, the solid substance obtained is stirred for 10 minutes with 3 ml of methanol, the suspension is cooled to 0° and the pure product is filtered off and dried in vacuo.

TLC: [chloroform/methanol (85:15)] $R_f$ 0.76
[chloroform/methanol/water (14:6:1)] $R_f$ 0.94.

STAGE 4.3

H-Asn-Phe-Phe-(D-trp)-Lys(Boc)-Thr(But)-Phe-[d,l-β-(3-phenoxyphenyl)]Gaba-OH

After the addition of 100 mg of palladium-on-carbon (10%), a solution of 943 mg of Z-Asn-Phe-Phe-(D-trp)-Lys(Boc)-Thr(But)-Phe-[d,l-β-(3-phenoxyphenyl)-]Gaba-OBzl (stage 4.2) in 30 ml of dimethylformamide is hydrogenated for 4 hours at room temperature under normal pressure. For working up, the solution is concentrated to 2 ml in a high vacuum after filtering off the catalyst and the product is precipitated with 40 ml of peroxide-free ether, filtered off and dried in vacuo. The crude product is subjected to the next stage 4.4 (cyclisation) without further purification.

STAGE 4.4

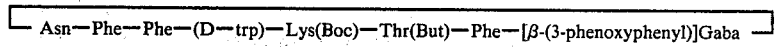
Asn—Phe—Phe—(D—trp)—Lys(Boc)—Thr(But)—Phe—[β-(3-phenoxyphenyl)]Gaba

A solution of 811 mg of crude H-Asn-Phe-Phe-(D-trp)-Lys(Boc)-Thr(But)-Phe-[d,l-β-(3-phenoxyphenyl)-]Gaba—OH (stage 4.3), 784 mg of N-hydroxybenzotriazole and 1.20 g of DCCI in 580 ml of dimethylformamide is maintained at 50° for 20 hours. For working up, the solvent is evaporated off in a high vacuum at approximately 30° and the residue is triturated with 20 ml of ethyl acetate. The precipitated dicyclohexylurea is removed by filtration, the filtrate is diluted with ethyl acetate to 200 ml, washed three times with 50 ml of 1 N aqueous oxalic acid each time and then with water until neutral, dried over sodium sulphate and concentrated by evaporation in vacuo. For purification, the crude product is subjected to countercurrent distribution over 600 stages in the system methanol/water/chloroform/-carbon tetrachloride (2700:675:900:1575 parts by volume). The phases found in units 80 to 113 (K=0.17) contain one of the two diastereoisomers (isomer A) and the phases found in units 125 to 167 (K=0.31) contain the other (isomer B). The phases of the corresponding units are combined and concentrated by evaporation in vacuo. The residue is dissolved in 20 ml of tert.-butanol and lyophilised whereby in each case a diastereoisomer of the above common formula is formed that is uniform according to thin layer chromatography.

TLC: [chloroform/methanol (85:15)] isomer A: $R_f$ 0.60;
isomer B: $R_f$ 0.51
[chloroform/methanol/water (14:6:1)]
isomer A: $R_f$ 0.89
isomer B: $R_f$ 0.83.

EXAMPLE 5

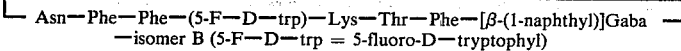
Asn—Phe—Phe—(5-F—D—trp)—Lys—Thr—Phe—[β-(1-naphthyl)]Gaba
—isomer B (5-F—D—trp = 5-fluoro-D—tryptophyl)

147 mg of protected octapeptide of the formula

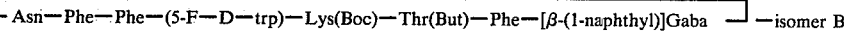
Asn—Phe—Phe—(5-F—D—trp)—Lys(Boc)—Thr(But)—Phe—[β-(1-naphthyl)]Gaba —isomer B are dissolved at 5° under $N_2$ in 2.5 ml of a mixture of 89% by volume of trifluoroacetic acid, 10% by volume of water and 1% by volume of thioglycolic acid; the solution is immediately heated to 25° and precipitated with 15 ml of peroxide-free ether after 50 minutes at this temperature. The resulting crude trifluoroacetate of the end product is filtered off, dried in vacuo, dissolved in 5 ml of 1 N acetic acid and filtered through 15 ml of an anion exchanger, for example AG ® 1-X8 (a product of Bio-Rad Laboratories, Richmond, Calif., USA), in acetate form. The eluate is concentrated by evaporation in vacuo and the residue is subjected to countercurrent distribution over 230 stages in the system n-butanol/acetic acid/water (4:1:5). The phases found in units 230 to 274 (K=13.7) are collected, concentrated by evaporation in vacuo and lyophilised from tert.-butanol/water (1:1).

The resulting title compound is uniform in three systems according to thin layer chromatography.

| TLC: system 52 | : | $R_f$ 0.50 |
|---|---|---|
| 111B: | | $R_f$ 0.45 |
| 157F: | | $R_f$ 0.55. |

The peptide starting material may be obtained in the following manner:

STAGE 5.1

Z-Asn-Phe-Phe-(5-F-D-trp)-Lys(Boc)-Thr(But)-Phe-[d,l-$\beta$-(1-naphthyl)]Gaba-OBzl 0.039 ml of N-methylmorpholine, 47 mg of N-hydroxybenzotriazole and 85 mg of DCCI are added to a mixture of 411 mg of Z-Asn-Phe-Phe-(5-F-D-trp)-Lys(Boc)-Thr(But)-Phe—OH (cf. stage 11.5, Example 11 of the initially mentioned European Patent Application) and 172 mg of d,l-4-amino-3-(1-naphthyl)-butyric acid benzyl ester p-toluenesulphonate (stage 2.1) in 3 ml of dimethylformamide and left to stand for 20 hours at room temperature. For working up, the precipitated DCC is centrifuged off, 10 ml of water are added to the supernatant liquid and filtration is effected. For further purification, the solid substance obtained is stirred with 2 ml of methanol for 10 minutes, the suspension is cooled to 0° and the pure product is filtered off and dried in vacuo.

| TLC: | [chloroform/methanol (85:15)] | $R_f$ 0.67 |
|---|---|---|
| | [chloroform/methanol/water (14:6:1)] | $R_f$ 0.87. |

STAGE 5.2

H-Asn-Phe-Phe-(5-F-D-trp)-Lys(Boc)-Thr(But)-Phe-[d,l-$\beta$-(1-naphthyl)]Gaba—OH After the addition of 50 mg of palladium-on-carbon (10%), a solution of 421 mg of Z-Asn-Phe-Phe-(5-F-D-trp)-Lys(Boc)-Thr(But)-Phe-[d,l-$\beta$-(1-naphthyl)]Gaba-OBzl (stage 5.1) in 15 ml of dimethylformamide is hydrogenated for 4 hours at room temperature under normal pressure. For working up, the solution is concentrated to 2 ml in a high vacuum after filtering off the catalyst and the product is precipitated with 40 ml of peroxide-free ether, filtered off and dried in vacuo. The crude product is subjected to the next stage 5.3 (cyclisation) without further purification.

STAGE 5.3

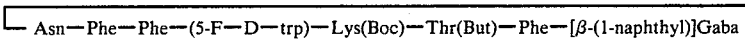

A solution of 357 mg of crude H-Asn-Phe-Phe-(5-F-D-trp)-Lys(Boc)-Thr(But)-Phe-[d,l-$\beta$-(1-naphthyl)]Gaba—OH (stage 5.2), 355 mg of N-hydroxybenzotriazole and 543 mg of DCCI in 260 ml of dimethylformamide is maintained at 50° for 20 hours. For working up, the solvent is evaporated off in a high vacuum at approximately 30° and the residue is triturated with 20 ml of ethyl acetate. The precipitated dicyclohexylurea is removed by filtration, the filtrate is diluted to 200 ml with ethyl acetate, washed three times with 50 ml of 1 N aqueous oxalic acid each time and then with water until neutral, dried over sodium sulphate and concentrated by evaporation in vacuo. For purification, the crude product is subjected to countercurrent distribution over 480 stages in the system methanol/water/chloroform/carbon tetrachloride (2700:675:900:1575 parts by volume). The phases found in units 75 to 114 (K=0.24) contain one of the two diastereoisomers (isomer A) and the phases found in units 161 to 186 (K=0.50) contain the other (isomer B). The phases of the corresponding units are combined and concentrated by evaporation in vacuo. The residue is dissolved in 20 ml of tert.-butanol and lyophilised whereby in each case a diastereoisomer of the above common formula is formed that is uniform according to thin layer chromatography.

| TLC: | [chloroform/methanol (85:15)] | isomer A | : | $R_f$ 0.54; |
|---|---|---|---|---|
| | | isomer B | : | $R_f$ 0.45 |
| | [chloroform/methanol/water (14:6:1)] | isomer A | : | $R_f$ 0.90; |
| | | isomer B | : | $R_f$ 0.85. |

EXAMPLE 6

178 mg of protected octapeptide of the formula

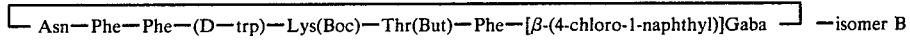 —isomer B are processed in exactly the same manner as described in Example 1B. The product is purified by countercurrent distribution over 770 stages in the system tert.-butanol/toluene/methanol/buffer (800:800:340:1140) (buffer containing 2.2 g of ammonium acetate and 1.6 ml of glacial acetic acid in 1 liter of water). The phases containing the pure isomer B (K=1.1) are concentrated by evaporation in vacuo and the residue is lyophilised from tert.-butanol/water.

| TCL: | system | 52: $R_f$ 0.46 |
|---|---|---|
| | | 157C: $R_f$ 0.24. |

The following is obtained in an analogous manner:

└─ Asn—Phe—Phe—(D—trp)—Lys—Thr—Phe—[β-(4-nitrophenyl)]Gaba ─┘ —isomer B,
K = 0.33 (in the above solvent system),
TLC: system 157C: R$_f$ 0.28.

The peptide starting materials may be obtained in the following manner:

STAGE 6.1

H-Asn-Phe-Phe-(D-trp)-Lys(Boc)-Thr(But)-Phe—OH

After the addition of 300 mg of palladium-on-carbon (10%), a solution of 3.1 g of Z-Asn-Phe-Phe-(D-trp)-Lys(Boc)-Thr(But)-Phe—OH (manufactured according to stage 1.7, Example 1 of the initially mentioned European Patent Application) in 100 ml of dimethylformamide is hydrogenated for 2 hours. After filtering off the catalyst, the solution is concentrated to 20 ml in a high vacuum and is used in the next stage 6.2 without further purification.

STAGE 6.2

N$^\alpha$-2-trimethylsilylethoxycarbonyl-Asn-Phe-Phe-(D-trp)-Lys(Boc)-Thr(But)-Phe—OH 940 mg of 2-trimethylsilylethylsuccinimidyl carbonate

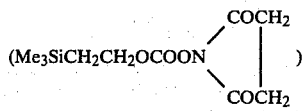

and 0.27 ml of N-methylmorpholine are added to the dimethylformamide solution of the protected heptapeptide obtained in stage 6.1 and allowed to react for 45 minutes at room temperature. After adding a further 0.13 ml of N-methylmorpholine the mixture is allowed to continue reacting for 2½ hours. The product is precipitated by adding the reaction mixture dropwise to 100 ml of 0.2 N hydrochloric acid at 0° C. and is purified by triturating three times with ethyl acetate and three times with acetonitrile.
TLC: system 157A: R$_f$ 0.29.

STAGE 6.3

N$^\alpha$-2-trimethylsilylethoxycarbonyl-Asn-Phe-Phe-(D-trp)-Lys(Boc)-Thr(But)-Phe-[d,1-β-(4-chloro-1-naphthyl)]Gaba—OH A solution of 216 mg of DCCI in 0.8 ml of dimethylformamide is added at 0° to a solution of 1.35 g of N$^\alpha$-2-trimethylsilylethoxycarbonyl-Asn-Phe-Phe-(D-trp)-Lys(Boc)-Thr(But)-Phe-OH (Stage 6.2) and 180 mg of N-hydroxysuccinimide in 2 ml of dimethylformamide and allowed to react for 4½ hours (part 1). In the meantime, 304 mg of d,1-4-amino-3-(4-chloro-1-naphthyl)-butyric acid are dissolved in 0.6 ml of 2 N benzyltrimethylammonium hydroxide in methanol with the addition of 10 ml of dimethylformamide and a little water and concentrated to 3.5 ml in a high vacuum. The turbid solution is added at 0° to the above part 1, washed twice with 0.2 ml of dimethylformamide each time and allowed to react overnight at room temperature. The product is precipitated by adding the reaction mixture dropwise to 100 ml of ice-cold 0.2 N hydrochloric acid and is then filtered off and washed with water. After drying, trituration is carried out three times with ethyl acetate and three times with acetonitrile.

TLC: system 157A: R$_f$ 0.39 and 0.41 (diastereoisomers).

N$^\alpha$-2-trimethylsilylethoxycarbonyl-Asn-Phe-Phe-(D-trp)-Lys(Boc)-Thr(But)-Phe-[d,1-β-(4-nitrophenyl)-]Gaba—OH is obtained in an analogous manner starting from d,1-4-amino-3-(4-nitrophenyl)-butyric acid;
TLC: system 157A: R$_f$ 0.37.

STAGE 6.4

H-Asn-Phe-Phe-(D-trp)-Lys(Boc)-Thr(But)-Phe-[d,1-β-(4-chloro-1-naphthyl)]Gaba—OH. hydrochloride 8.6 ml of a 0.59 M solution of tetraethylammonium fluoride in dimethyl sulphoxide are added at 0° in the course of 2 minutes to a solution of 1.55 g of N$^\alpha$-2-trimethylsilylethoxycarbonyl-Asn-Phe-Phe-(D-trp)-Lys(Boc)-Thr(But)-Phe-[d,1-β-(4-chloro-1-naphthyl)-]Gaba—OH (stage 6.3) in 4.2 ml of dimethylformamide and allowed to react for 3 hours at 30°. The product is precipitated by adding the reaction mixture dropwise to 200 ml of ice-cold 0.1 N hydrochloric acid. The precipitate is centrifuged off, washed with ice-cold water, dissolved in tert.-butanol and lyophilised. The residue is dissolved in 3 ml of dimethylformamide and precipitated with water. The product isolated by centrifugation is washed several times with water and dried in a high vacuum.

TLC: system 157A: R$_f$ 0.09 and 0.12 (diastereoisomers).

H-Asn-Phe-Phe-(D-trp)-Lys(Boc)-Thr(But)-Phe-[d,1-β-(4-nitrophenyl)]Gaba—OH. hydrochloride is obtained in an analogous manner from the corresponding starting material (cf. stage 6.3).

TLC: system 157C: R$_f$ 0.53 and 0.55 (diastereoisomers).

STAGE 6.5

└─Asn—Phe—Phe—(D—trp)—Lys(Boc)—Thr(But)—Phe—[β-(4-chloro-1-naphthyl)]Gaba─┘ —isomer B.

A solution of 1.25 g of HCl.H-Asn-Phe-Phe-(D-trp)-Lys(Boc)-Thr(But)-Phe-[d,1-β-(4-chloro-1-naphthyl)-]Gaba—OH (stage 6.4), 1.33 g of N-hydroxybenzotriazole monohydrate, 0.1 ml of N-methylmorpholine and 1.8 g of DCCI in 800 ml of dimethylformamide is maintained at 50° for 18 hours. For working up, 1.1 g of oxalic acid are added, the solution is concentrated to a great extent in a high vacuum and the precipitated dicyclohexylurea is removed by filtration. The filtrate is precipitated by adding dropwise to dilute sodium bicarbonate solution. For purification, the crude product is subjected to countercurrent distribution over 560 stages in the system methanol/water/chloroform/carbon tetrachloride (2700:675:900:1575 parts by volume). The product found in units 154 to 228 (K=0.43) is isolated in the usual manner-isomer B:

TLC: system 157A: R$_f$ 0.33.

In an analogous manner,

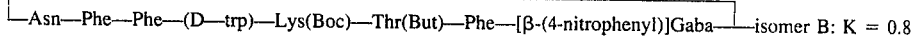

is obtained from the corresponding linear starting material (cf. stage 6.4) by cyclisation and subsequent countercurrent distribution in the same solvent system. TLC: system 157A: $R_f 0.27$.

The following Examples 7 to 13 illustrate the manufacture of pharmaceutical forms of medication. The term "active substance" refers to the end products of the formula I obtainable according to the invention, especially to those of Examples 1 to 6 and more especially to [D-Trp$^8$; β-(1-naphthyl)Gaba$^{12}$]-cyclosomatostatin(5-12)-octapeptide-isomer B of Example 2B and [D-Trp$^8$; β-(3-phenoxyphenyl)Gaba$^{12}$]-cyclosomatostatin(5-12)-octapeptide of Example 4B.

EXAMPLE 7

(A) An injection solution containing 2.0 mg of active substance is obtained in the following manner:

1.0 mg of glacial acetic acid, 0.8 mg of sodium acetate, 8.0 mg of sodium chloride and 2.0 mg of active substance are dissolved in 0.7 ml of distilled water and the volume is made up to 1 ml with distilled water. The solution is heated for 20 minutes in an autoclave at 120°. After sterilisation the pH is 4.5.

(B) An injection solution containing 0.5 mg of the active substance is obtained in the following manner:

0.5 mg of active substance is dissolved in 0.7 ml of physiological sodium chloride solution and the solution is acidified with 0.1 N hydrochloric acid to pH 4.0. The volume is made up to 1 ml with distilled water and the mixture is filtered under sterile conditions.

EXAMPLE 8

(A) A gelatin-containing injection solution containing 0.1 mg of active substance is obtained in the following manner:

An aqueous solution of the active substance that has been filtered under sterile conditions is mixed, while heating, under aseptic conditions with a sterile gelatin solution, containing phenol as a preservative; so that 1.0 ml of solution has the following composition:

| active substance | 0.1 | mg |
|---|---|---|
| gelatin | 150.0 | mg |
| phenol | 4.7 | mg |
| distilled water to make up to | 1.0 | ml. |

The mixture is poured under aseptic conditions into 1.0 ml phials.

(B) An analogous injection solution containing 0.5 mg of the active substance is obtained in the same manner as indicated above by producing a mixture having the following composition:

| active substance | 0.5 | mg |
|---|---|---|
| gelatin | 280.0 | mg |
| phenol | 5.0 | mg |
| distilled water to make up to | 1.0 | ml. |

The mixture is poured under aseptic conditions into 1.0 ml phials.

EXAMPLE 9

A preparation, containing 0.5 mg of active substance, as a sterile dry substance for injection is obtained in the following manner: 0.5 mg of active substance is dissolved in 1 ml of an aqueous solution of 20 mg of mannitol. The solution is filtered under sterile conditions and poured under aseptic conditions into a 2 ml ampoule, deep-frozen and lyophilised. Before use, the lyophilisate is dissolved in distilled water. The solution is administered intramuscularly or intravenously.

EXAMPLE 10

An injection preparation containing the active substance as a polyphosphate suspension is obtained in the following manner:

(A) With 1.0 mg of active substance:

A solution of 1.0 mg of active substance and 9.0 mg of sodium chloride in 0.5 ml of distilled water is mixed with a solution of 2 mg of sodium polyphosphate (Calgon N ®) in 0.5 ml of distilled water. The suspension obtained has the following composition:

| active substance | 1.0 | mg |
|---|---|---|
| sodium polyphosphate (Calgon N ®) | 2.0 | mg |
| sodium chloride | 9.0 | mg |
| distilled water to make up to | 1.0 | ml. |

The suspension has a pH of 6.9. It is suitable for intramuscular administration.

(B) With 0.5 mg of active substance:

In the same manner as indicated above, a suspension having the following composition is produced:

| active substance | 0.5 | mg |
|---|---|---|
| sodium polyphosphate (Calgon 322 ®) | 1.0 | mg |
| sodium chloride | 9.0 | mg |
| distilled water to make up to | 1.0 | ml. |

The pH of the suspension is 5.9.

EXAMPLE 11

Injection preparation containing 0.3 mg of active substance in the form of an oily aluminium stearate gel A 2% aluminium stearate gel is prepared in the usual manner by suspending 1.0 g of aluminium monostearate in 49.0 g of peanut oil and then heating at 130° for 10 minutes. 15.0 mg of active substance are suspended in 0.3 g of the above aluminium stearate gel, homogenised and diluted with the remaining quantity of the aluminium stearate gel. The gel so obtained has the following composition:

| active substance | 0.3 | mg |
|---|---|---|
| aluminium monostearate | 20.0 | mg |
| peanut oil to make up to | 1.0 | ml. |

The oily aluminium stearate gel suspension is suitable for intramuscular administration.

EXAMPLE 12

Injection preparation containing 0.5 mg of active substance as a depot suspension with dextran sulphate 0.36 mg of acetic acid, 1.9 mg of sodium acetate trihydrate, 8.0 mg of sodium chloride and 0.5 mg of active substance are dissolved in 0.4 ml of distilled water and the volume is made up to 0.5 ml with distilled water. 0.5 ml of a 0.1% solution of dextran sulphate (molecular weight 500,000) is added to this solution while stirring, a homogeneous precipitate being formed. The suspension obtained has the following composition:

| | | |
|---|---|---|
| active substance | 0.50 | mg |
| dextran sulphate MW 500,000 | 0.50 | mg |
| acetic acid 100% | 0.36 | mg |
| sodium acetate trihydrate | 1.90 | mg |
| sodium chloride | 8.00 | mg |
| distilled water to make up to | 1.00 | ml |

The aqueous suspension is suitable for intramuscular and subcutaneous injection.

EXAMPLE 13

Nasal spray 30 mg of finely ground active substance are suspended in a mixture of 75 mg of benzyl alcohol and 1.395 g of a mixture of semi-synthetic glycerides of saturated fatty acids having 8 to 12 carbon atoms (for example Miglyol ® 812). This suspension is placed in aluminium monobloc containers (content 10 ml) that are then closed with a metering valve and 6.0 g of a mixture of dichlorodifluoromethane and 1,2-dichloro-1,1,2,2-tetrafluoroethane (for example Freon ® 12/114) in the ratio of 40:60 by volume are added under nitrogen pressure. The aluminium container having a total charge of 7.5 g contains 100 individual doses each containing 0.3 mg of active substance. The spray container is so adjusted by means of the alive that a single dose is sprayed by pressing once.

Nasal sprays that contain, instead of the Miglyol ®, the same quantity by weight of isopropyl myristate or isopropyl palmitate or a mixture of glycerol and polyoxyethylene glycol esters of fatty acids having 8 and 10 carbon atoms (for example Labrafac ® WL 1219) are manufactured in the same manner.

We claim:

1. A cyclic octapeptide of the formula

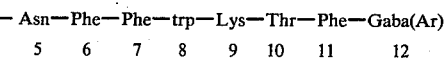

$$\text{Asn—Phe—Phe—trp—Lys—Thr—Phe—Gaba(Ar)} \quad (I)$$
$$\phantom{\text{Asn—}}5\phantom{\text{he—}}6\phantom{\text{—Ph}}7\phantom{\text{—tr}}8\phantom{\text{—Ly}}9\phantom{\text{—Th}}10\phantom{\text{—Ph}}11\phantom{\text{—Ga}}12$$

in which trp represents D-Trp, and
Gaba(Ar) represents the residue of a γ-amino-butyric acid substituted in the β-position by cyclohexyl, phenyl or naphthyl or by a phenyl or naphthyl which is substituted by halogen, nitro or phenoxy, a pharmaceutically acceptable acid addition salt and a complex thereof.

2. A compound according to claim 1, in which trp represents D-Trp and Gaba(Ar) represents the residue of 4-amino-3-cyclohexylbutyric acid, 4-amino-3-phenyl-butyric acid, 4-amino-3-(1-naphthyl)-butyric acid or 4-amino-3-(2-naphthyl)-butyric acid, in the form of a diastereoisomeric mixture or of an individual diastereoisomer, a pharmaceutically acceptable acid addition salt and a complex thereof.

3. Isomer B of a compound defined in claim 2, which is defined as the diastereoisomer derived from the more hydrophilic component obtained by the countercurrent distribution of a diastereoisomer mixture of a corresponding derivative having the -Lys$^9$- and/or -Thr$^{10}$- residue in a protected form.

4. A compound according to claim 1, in which trp represents D-Trp and Gaba(Ar) represents the residue of 4-amino-3-(4-fluorophenyl)-butyric acid, 4-amino-3-(4-nitrophenyl)-butyric acid, 4-amino-3-(4-chloro-1-naphthyl)-butyric acid or 4-amino-3-(3-phenoxyphenyl)-butyric acid, in the form of a diastereoisomeric mixture or of an individual diastereoisomer, a pharmaceutically acceptable acid addition salt and a complex thereof.

5. Isomer B of a compound defined in claim 4, which is defined as the diastereoisomer derived from the more hydrophilic component obtained by the countercurrent distribution of a diastereoisomer mixture of a corresponding derivative having the -Lys$^9$- and/or -Thr$^{10}$- residue in a protected form.

6. [D-Trp$^8$; β-cyclohexyl-Gaba$^{12}$]-cyclosomatostatin(5–12)-octapeptide, in the form of a diastereoisomeric mixture or of an individual diastereoisomer, a pharmaceutically acceptable acid addition salt and a complex thereof.

7. Isomer B of a compound defined in claim 6, which is defined as the diastereoisomer derived from the more hydrophilic component obtained by the countercurrent distribution of a diastereoisomer mixture of a corresponding derivative having the -Lys$^9$- and/or -Thr$^{10}$- residue in a protected form.

8. [D-Trp$^8$; β-(3-phenoxyphenyl)-Gaba$^{12}$]-cyclosomatostatin(5–12)-octapeptide, in the form of a diastereoisomeric mixture or of an individual diastereoisomer, a pharmaceutically acceptable acid addition salt and a complex thereof.

9. Isomer B of a compound defined in claim 8, which is defined as the diastereoisomer derived from the more hydrophilic component obtained by the countercurrent distribution of a diastereoisomer mixture of a corresponding derivative having the -Lys$^9$- and/or -Thr$^{10}$- residue in a protected form.

10. [D-Trp$^8$; β-(1-naphthyl)-Gaba$^{12}$]-cyclosomatostatin(5–12)-octapeptide, in the form of a diastereoisomeric mixture or of an individual diastereoisomer, a pharmaceutically acceptable acid addition salt and a complex thereof.

11. Isomer B of a compound defined in claim 10, which is defined as the diastereoisomer derived from the more hydrophilic component obtained by the countercurrent distribution of a diastereoisomer mixture of a corresponding derivative having the -Lys$^9$- and/or -Thr$^{10}$-residue in a protected form.

12. A pharmaceutical preparation for treating, in mammals, diabetes or blood losses in gastro-intestinal tract containing an effective amount of at least one of the compounds according to any one of claims 1 to 11 in combination with at least one pharmaceutically acceptable excipient.

13. A method of treating, in mammals, diabetes or blood losses in the gastro-intestinal tract, which method comprises administering to said mammal a compound defined in any one of claims 1 to 11 in an amount sufficient to effect, in said mammal, an anti-diabetic response or, respectively, to prevent blood losses.

14. A compound of the formula

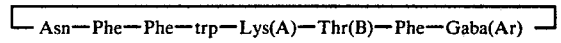 (II)

in which
- trp represents [L-Trp or] D-Trp, and
- Gaba(Ar) represents the residue of a γ-amino-butyric acid substituted in the β-position by cyclohexyl, phenyl or naphthyl, or by a phenyl or naphthyl which is substituted by halogen, nitro or phenoxy,
- A represents an γ-amino-protecting group or hydrogen and
- B represents a hydroxyl-protecting group or hydrogen, it being possible for only one of the symbols A and B to represent hydrogen, and an acid addition salt thereof.

15. A linear peptide of the formula

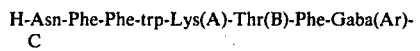 (IIIb)

in which
- trp represents D-Trp,
- Gaba(Ar) represents the residue of a γ-amino-butyric acid substituted in the β-position by cyclohexyl, phenyl or naphthyl, or by a phenyl or naphthyl which is substituted by halogen, nitro or phenoxy,
- A represents an ε-amino-protecting group or hydrogen,
- B represents a hydroxyl-protecting group or hydrogen, it being possible for only one of the symbols A and B to represent hydrogen, and
- C represents a free hydroxyl group, a hydroxyl group modified by an activating group or represents the hydrazino group —NH—NH$_2$, and a acid addition salt thereof.

* * * * *